(12) United States Patent
Wang

(10) Patent No.: US 9,730,826 B2
(45) Date of Patent: Aug. 15, 2017

(54) HAND BRACE

(71) Applicant: Meng-Chun Wang, Taichung (TW)

(72) Inventor: Meng-Chun Wang, Taichung (TW)

(*) Notice: Subject to any disclaimer, the term of this patent is extended or adjusted under 35 U.S.C. 154(b) by 247 days.

(21) Appl. No.: 14/665,424

(22) Filed: Mar. 23, 2015

(65) Prior Publication Data

US 2016/0058602 A1 Mar. 3, 2016

(30) Foreign Application Priority Data

Aug. 27, 2014 (TW) .............................. 103215342 U

(51) Int. Cl.
*A61F 5/00* (2006.01)
*A61F 5/058* (2006.01)

(52) U.S. Cl.
CPC ................................ *A61F 5/05866* (2013.01)

(58) Field of Classification Search
CPC ...... B41B 7/16; A61F 5/0118; A61F 5/05875; A61F 5/05866; A61F 5/10; A61F 2005/0179; A61F 5/01; A61F 5/028; A61F 13/108; A61F 2005/0137; A61F 2005/0153; A61F 2005/0197; A61F 2/08; A61F 2/0811; A61F 2/583; A61F 5/013; A61F 5/3761; A61F 2002/7615; A61F 2/586; A61F 5/05858; A61F 5/0585; A61F 5/058; A61F 13/10; A61F 13/105; A61F 13/107; A61H 1/0285; A61H 1/0288; A61H 2201/0107; A61H 2201/1215; A61H 2201/123; A61H 2201/1246; A61H 2201/149; A61H 2201/1638; A61H 2201/165; A61H 2201/169; A61H 2201/1697; A61H 2205/065; A61H 1/0274; A61H 2201/1635; A61H 2201/16; A61H 2205/06; A61H 2205/067; A61H 2205/00; A47B 2021/0307; A47B 21/0371; A61B 17/00491; A61B 17/0057; A61B 17/12022; A61B 17/12118; A61B 17/12181; A61B 17/3468; A61B 18/02; A61B 18/04; A61B 18/1492; A61B 18/18; A61B 18/245; A61B 17/24; A61B 17/32002; A61B 1/00147; A61B 1/015; A61B 1/12; A61B 1/233; A01B 63/145; A01B 63/1117; A01D 34/64; A01D 46/28; A61G 7/001; A61G 7/002;

(Continued)

(56) References Cited

U.S. PATENT DOCUMENTS

| 3,714,940 A * | 2/1973 | Palmer | A61F 5/10 602/21 |
| 8,784,348 B2 * | 7/2014 | Farrell | A61F 5/05866 602/20 |
| 2013/0072829 A1 * | 3/2013 | Fausti | A61H 1/0285 601/40 |

* cited by examiner

*Primary Examiner* — Victoria J Hicks
(74) *Attorney, Agent, or Firm* — Muncy, Geissler, Olds & Lowe, P.C.

(57) ABSTRACT

A hand brace includes a wrist sheath and a finger holder. The finger holder has a height adjusting rod, a length adjusting rod, and a finger support. The height adjusting rod has one end pivotally connected to the wrist sheath, so that the height adjusting rod is allowed to adapt to a wearer's finger in terms of position. The length adjusting rod is connected to an opposite end of the height adjusting rod in an axially movable manner, so that the length adjusting rod is allowed to adapt to the wearer's finger in terms of length. The length adjusting rod has a joint portion that has pivotal connection with the finger support. Thereby, the hand brace provides the wearer's finger with sufficient and relevant support.

9 Claims, 7 Drawing Sheets

(58) Field of Classification Search
CPC .......... A61G 7/008; A61G 7/015; A61G 7/02;
A61G 7/0526; A61G 7/065; A61G 7/07
USPC .................. 602/16, 20–22; 128/878, 880
See application file for complete search history.

HAND BRACE

BACKGROUND OF THE INVENTION

1. Technical Field

The present invention relates to medical aids, and more particularly to a hand brace.

2. Description of Related Art

For helping those having injured wrists, fingers or palms to recover as soon as possible, hand braces are usually used to protect the injured portions from secondary injury by supporting and holding the injured portions in position.

However, the existing hand braces are typically made with fixed dimensions and are not adaptive to wearers' individual palms and fingers in terms of both size and position. This limitation makes the protection provided by the existing hand braces highly restricted.

BRIEF SUMMARY OF THE INVENTION

The primary objective of the present invention is to provide a hand brace that can be positionally adjusted according to wearers' needs, so as to provide excellent support and practicality.

For achieving the foregoing objective, the disclosed hand brace comprises a wrist sheath and a finger holder. The finger holder has a height adjusting rod, a length adjusting rod, and a finger support. The height adjusting rod has one end pivotally connected to the wrist sheath, so that the height adjusting rod is allowed to adapt to a wearer's finger in terms of position. The length adjusting rod is connected to an opposite end of the height adjusting rod in an axially movable manner, so that the length adjusting rod is allowed to adapt to the wearer's finger in terms of length. Furthermore, the length adjusting rod has a joint portion. The finger support is pivotally connected to the joint portion of the length adjusting rod for supporting a wearer's injured finger. Thereby, the hand brace can adapt to fingers having different lengths and injured sites, so as to provide excellent support and practicality.

In one embodiment of the present invention, the wrist sheath has a seat. The seat has a first threaded hole and a first positioning toothed portion arranged around the first threaded hole. The height adjusting rod has one end provided with a first through hole and a second positioning toothed portion arranged around the first through hole. The second positioning toothed portion engages with the first positioning toothed portion of the seat of the wrist sheath. The height adjusting rod and the seat are pivotally connected through a first bolt. The first bolt passes through the first through hole of the height adjusting rod and is screwed into the first threaded hole of the seat of the wrist sheath. Thereby, when the first bolt is unscrewed, the height adjusting rod is allowed to have height adjustment with respect to the wrist sheath.

In one embodiment of the present invention, the height adjusting rod has a first rod and a second rod. The first rod has one end provided with the first through hole and the second positioning toothed portion, and an opposite end provided with a second threaded hole and a third positioning toothed portion arranged around the second threaded hole. The second rod has one end provided with a second through hole and a fourth positioning toothed portion arranged around the second through hole. The fourth positioning toothed portion engages with the third positioning toothed portion of the first rod. The first and second rods are pivotally connected through a second bolt. The second bolt is received in the second through hole of the second rod and is screwed into the second threaded hole of the first rod. Thereby, when the second bolt is unscrewed, the first and second rods can pivot with respect to each other for adjusting the use angle. When the second bolt is screwed to the end, the first and second rods are relatively positioned by means of the first and second positioning toothed portions.

In one embodiment of the present invention, the second rod of the height adjusting rod has a toothed hole and a third threaded hole that is radially communicated with the toothed hole. The height adjusting rod further has a third bolt. The third bolt is screwed into the third threaded hole of the second rod. The length adjusting rod also has a toothed shaft connected to the joint portion. The toothed shaft is received in the toothed hole in an axially movable manner. Thereby, when the third bolt is unscrewed, the length adjusting rod can move axially to provide length adjustment. When the third bolt is screwed to the end, the toothed shaft of the length adjusting rod is propped by the third bolt and thereby getting positioned.

In one embodiment of the present invention, the finger support has a cradle and a joint member, in which the cradle has one end provided with a third through hole and a fifth positioning toothed portion arranged around the third through hole, and the joint member has one end pivotally connected to the joint portion of the length adjusting rod, and an opposite end provided with a fourth threaded hole and a sixth positioning toothed portion arranged around the fourth threaded hole, the sixth positioning toothed portion engaging with the fifth positioning toothed portion of the cradle, the cradle being pivotally connected to the joint member through a fourth bolt, the fourth bolt passing through the third through hole of the cradle and being screwed into the fourth threaded hole of the joint member. Thereby, when the fourth bolt is unscrewed, the cradle is allowed to pivot on the joint member.

DETAILED DESCRIPTION OF THE INVENTION

Figure 1:
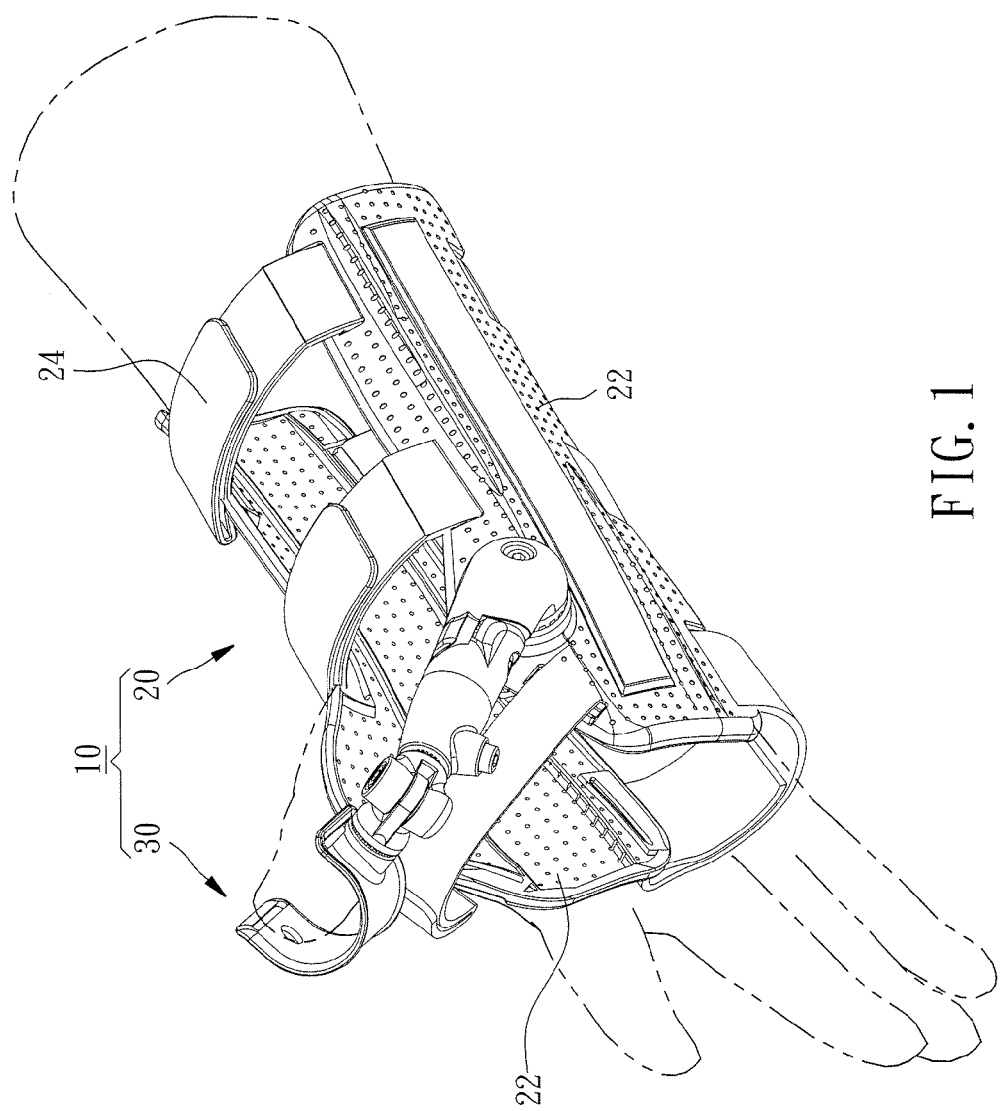
FIG. 1 is a perspective view of the present invention.
Figure 2:
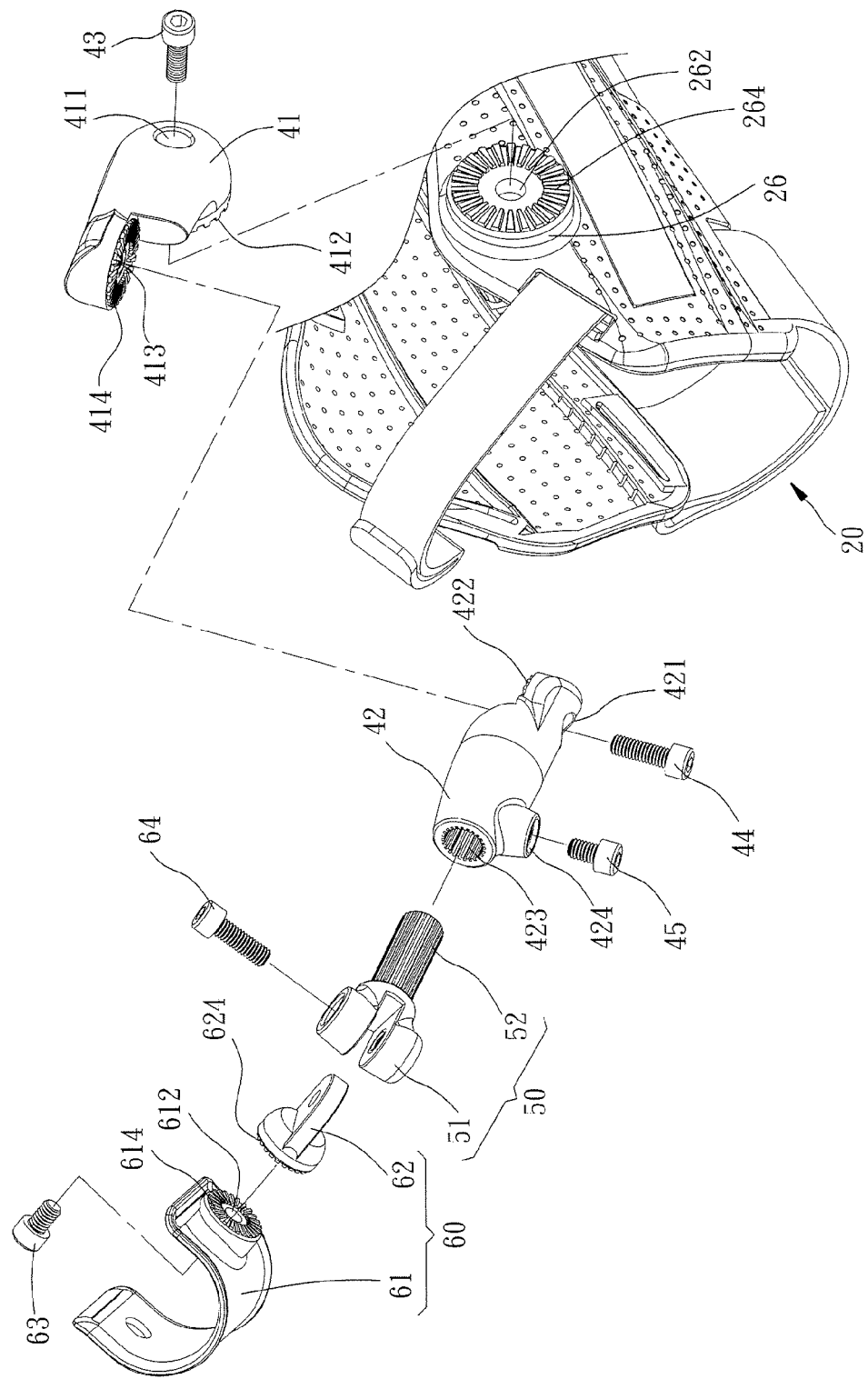
FIG. 2 is an exploded view of the present invention.
Figure 3:
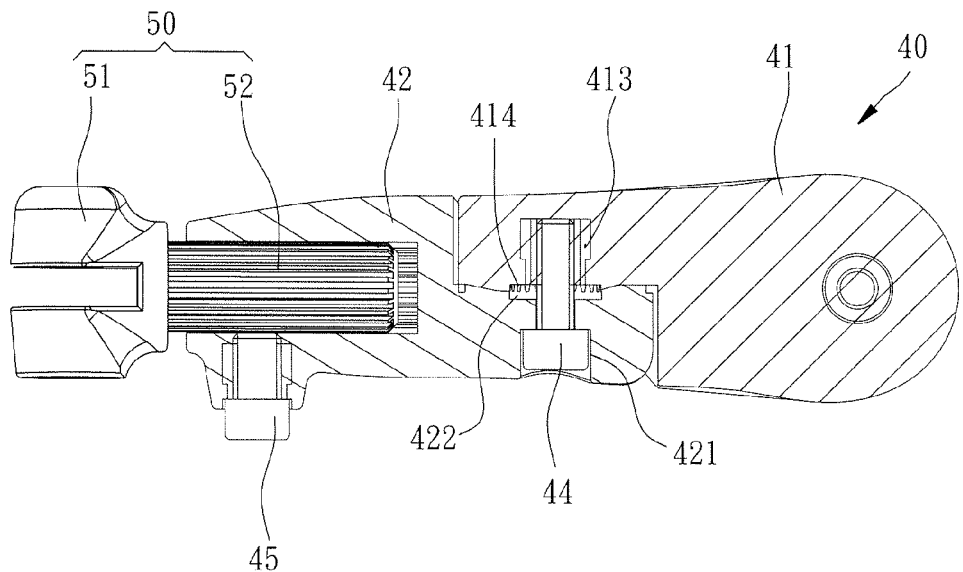
FIG. 3 is a partial, cross-sectional view of the present invention, showing the relation between the height adjusting rod and the length adjusting rod.
Figure 4:
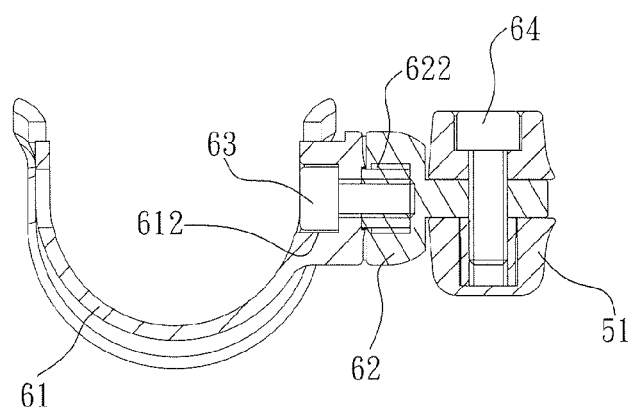
FIG. 4 is another partial, cross-sectional view of the present invention, showing the relation between the length adjusting rod and the finger support.

Referring to FIG. 1 and FIG. 2, according to the present invention, a hand brace 10 comprises a wrist sheath 20 and a finger holder 30.

The wrist sheath 20 has two pads 22 combined by plural touch fasteners 24 therebetween. The wrist sheath 20 further has a seat 26. The seat 26 is fixed to an outer lateral surface of one of the pads 22, and has a first threaded hole 262 and a first positioning toothed portion 264 arranged around the first threaded hole 262.

The finger holder 30 has a height adjusting rod 40, a length adjusting rod 50, and a finger support 60.

The height adjusting rod 40 includes a first rod 41, a second rod 42, a first bolt 43, a second bolt 44, and a third bolt 45. The first rod 41 has one end provided with a first through hole 411 and a second positioning toothed portion 412 arranged around the first through hole 411. The first rod 41 has an opposite end provided with a second threaded hole 413 and a third positioning toothed portion 414 arranged around the second threaded hole 413. The second rod 42 has one end provided with a second through hole 421 and a fourth positioning toothed portion 422 arranged around the second through hole 421. The second rod 42 has an opposite end provided with a toothed hole 423 and a third threaded hole 424 radially communicated with the toothed hole 423. The first bolt 43 passes through the first through hole 411 of the first rod 41 and is screwed into the first threaded hole 262 of the seat 26 of the wrist sheath 20. When the first bolt 43 is screwed to the end, the second positioning toothed portion 412 of the first rod 41 and the first positioning toothed portion 264 of the seat 26 of the wrist sheath 20 come to engage with each other, so that the first rod 41 is prevented from pivot on the wrist sheath 20. When the first bolt 43 is unscrewed, the first rod 41 is allowed to pivot on the wrist sheath 20. The second bolt 44 passes through the second through hole 421 of the second rod 42, and is screwed into the second threaded hole 413 of the first rod 41. When the second bolt 44 is screws to the end, the third positioning toothed portion 414 of the first rod 41 and the fourth positioning toothed portion 422 of the second rod 42 come to engage with each other, so that the first and second rods 41, 42 are prevented from relative rotation. When the second bolt 44 is unscrewed, the first and second rods 41, 42 are allowed to rotate with respect to each other. The third bolt 45 is screwed into the third threaded hole 424 of the second rod 42.

The length adjusting rod 50 has a joint portion 51 and a toothed shaft 52 connected to the joint portion 51. The length adjusting rod 50 is combined with the second rod 42 of the height adjusting rod 40 by means of the engagement between the toothed shaft 52 and the toothed hole 423. Thereby, when the third bolt 45 is not fastened, the length adjusting rod 50 is allowed to move axially along the toothed hole 423. When the third bolt 45 is screwed to the end, the third bolt 45 has its terminal propping against the toothed shaft 52 of the length adjusting rod 50, thereby positioning the length adjusting rod 50.

The finger support 60 includes a cradle 61, a joint member 62, and a fourth bolt 63. The cradle 61 has one end provided with a third through hole 612 and a fifth positioning toothed portion 614 arranged around the third through hole 612. The joint member 62 has one end pivotally connected to the joint portion 51 of the length adjusting rod 50 through a fifth bolt 64. The joint member 62 has an opposite end provided with a fourth threaded hole 622 and a sixth positioning toothed portion 624 arranged around the fourth threaded hole 622. Thereby, when the fifth bolt 64 is unscrewed, the included angle between the joint member 62 and the length adjusting rod 50 can be adjusted. The fourth bolt 63 passes through the third through hole 612 of the cradle 61 and is screwed into the fourth threaded hole 622 of the joint member 62. Thereby, when the fourth bolt 63 is screwed to the end, the fifth positioning toothed portion 614 of the cradle 61 and the sixth positioning toothed portion 624 of the joint member 62 come to engage with each other, so as to prevent the cradle 61 from pivot on the joint member 62. When the fourth bolt 63 is unscrewed, the cradle 61 is allowed to pivot on the joint member 62.

Figure 5:
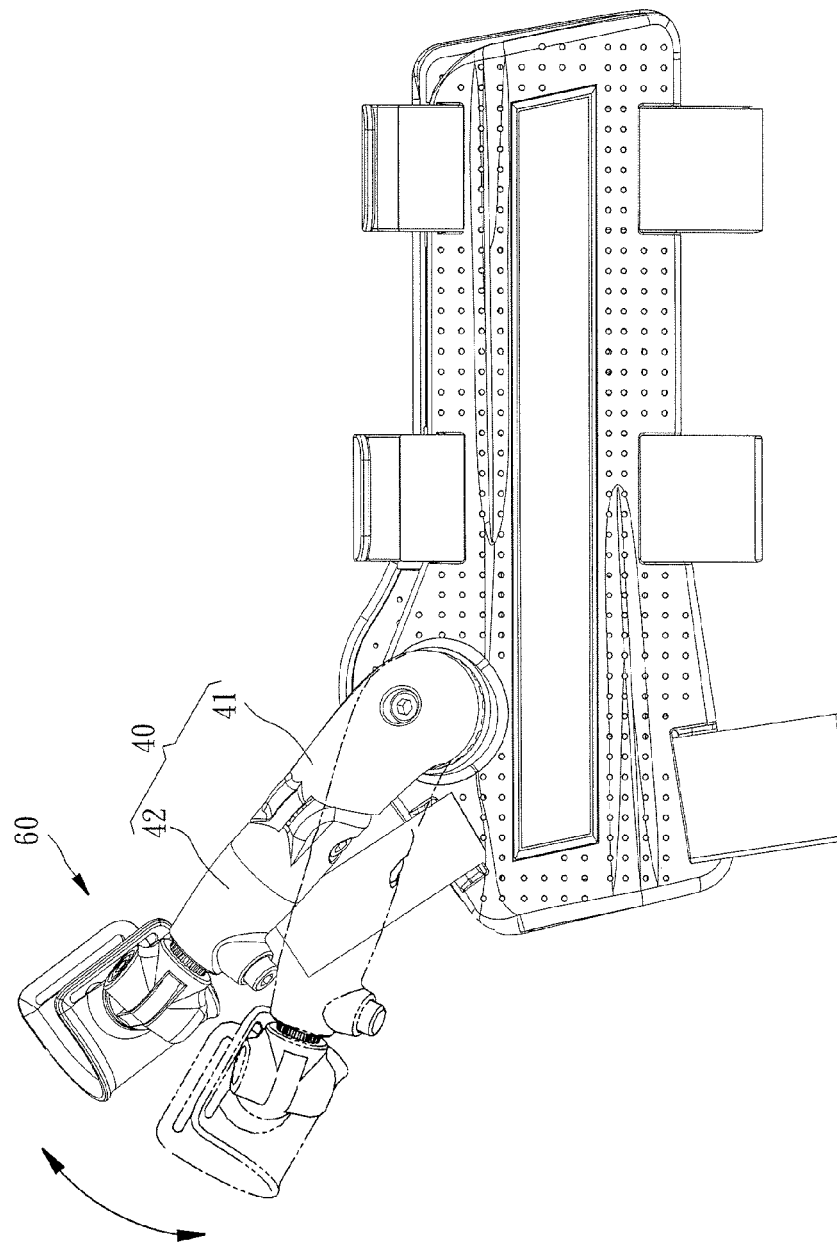
FIG. 5 is a side view of the present invention, showing the pivot of the height adjusting rod on the wrist sheath.
Figure 6:
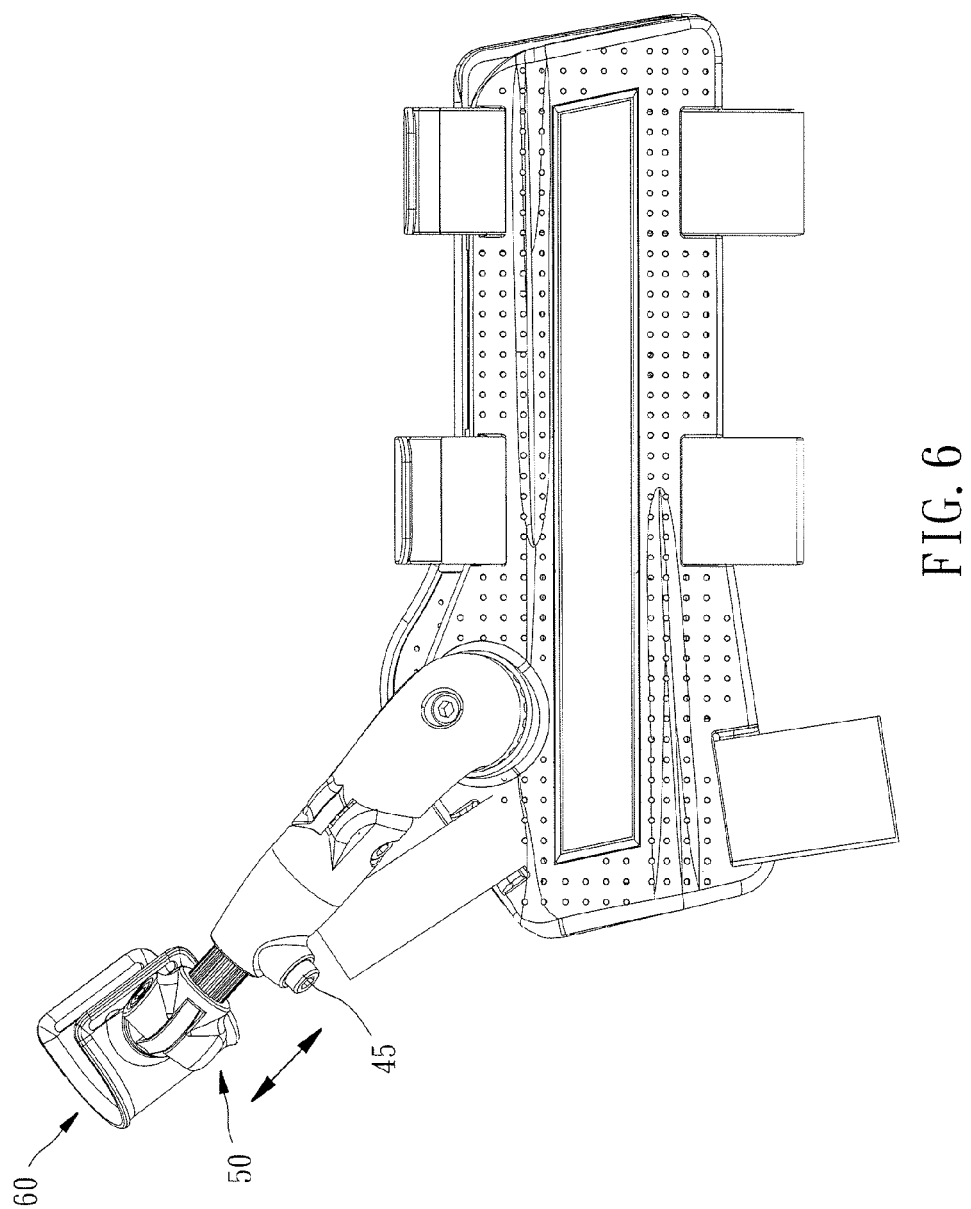
FIG. 6, similar to FIG. 5, showing the length adjusting rod extended.
Figure 7:
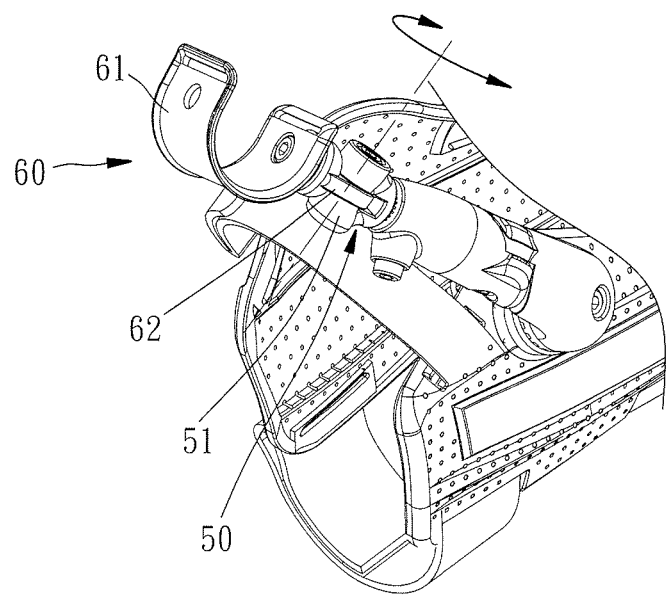
FIG. 7 is another side view of the present invention, shows the pivot between the joint member of the finger support and the length adjusting rod.

In an example of use, a wearer first place his/her wrist in the wrist sheath 20, and then unscrews the first bolt 43, so that the finger support 60 can be adjusted in terms of height according to his/her injured finger due to the height adjusting rod 40 (as shown in FIG. 5). After the adjustment, the wearer unscrews the third bolt 45 and pulls the length adjusting rod 50 outward (as shown in FIG. 6), so that the finger support 60 can be positioned according to the length of the injured finger. After the adjustment, the wearer screws the third bolt 45 to the end, and then unscrew the fifth bolt 64, so as to allow the finger support 60 to pivot on the joint member 62 with respect to the length adjusting rod 50 (as shown in FIG. 7), thereby allowing the cradle 61 of the finger support 60 to be properly positioned to support the finger joint of the injured finger.

Figure 8:
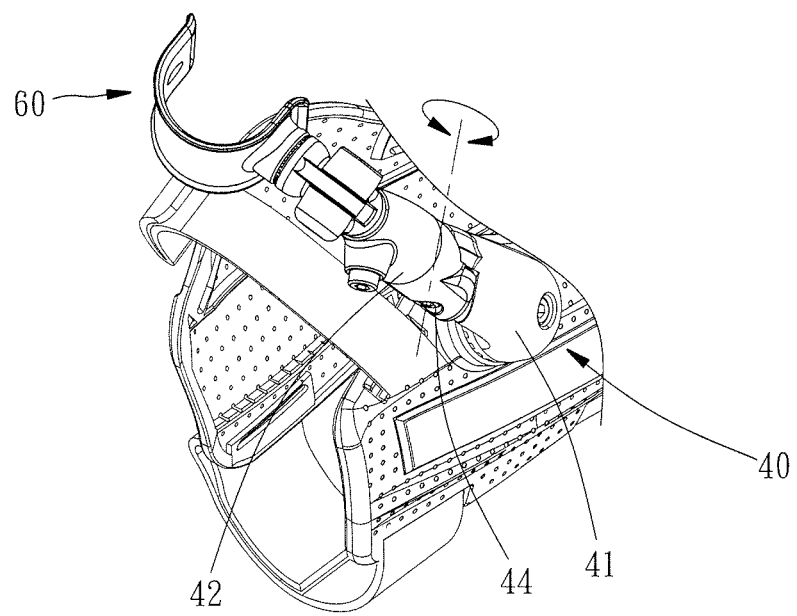
FIG. 8, similar to FIG. 7, shows the pivot between the first and second rods of the height adjusting rod.
Figure 9:
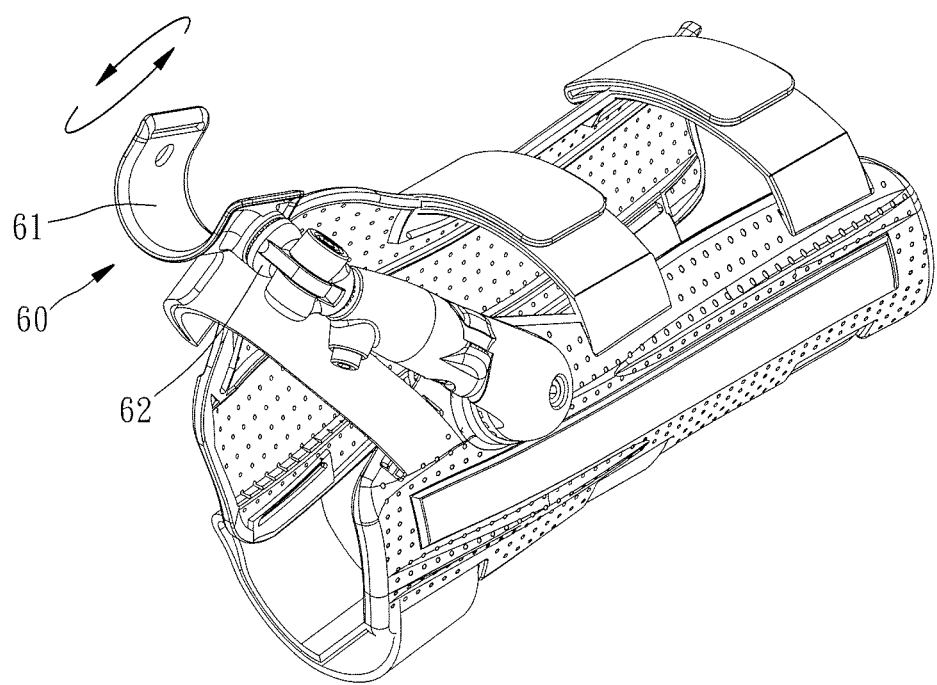
FIG. 9, similar to FIG. 1, shows the pivot between the cradle of the finger support and the joint member of the finger support.

It is to be noted that during the adjustment of the height adjusting rod 40, the second bolt 44 can be unscrews if necessary, so as to allow the first and second rods 41, 42 of the height adjusting rod 40 to rotate with respect to each other, as shown in FIG. 8, thereby providing fine tuning for the position of the finger support 60. Additionally, during the adjustment of the length adjusting rod 50, if necessary, the toothed shaft 52 can be fully withdrawn from the toothed hole 423 of the second rod 42 of the height adjusting rod 40, and rotate by a predetermined angle before being inserted into and reengaging with the toothed hole 423. This allows the angle between the length adjusting rod 50 and the second rod 42 of the height adjusting rod 40 to be changed. Moreover, during the adjustment of the finger support 60, the fourth bolt 63 can be unscrewed, so as to allow the cradle 61 of the finger support 60 to pivot on the joint member 62 of the finger support 60, as shown in FIG. 9, to a position most favorable to its support.

To sum up, the disclosed hand brace 10 features for a multi-joint structure. This structure adapts an injured finger in terms of both height and length, so as to provide excellent support and practicality.

What is claimed is:
1. A hand brace, comprising:
a wrist sheath; and
a finger holder, having a height adjusting rod, a length adjusting rod, and a finger support, the height adjusting rod having one end pivotally connected to an outer lateral surface of the wrist sheath, the length adjusting rod being connected to an opposite end of the height adjusting rod in an axially movable manner and having a joint portion, and the finger support being pivotally connected to the joint portion of the length adjusting rod;
wherein the wrist sheath has a seat that has a first threaded hole and a first positioning toothed portion arranged around the first threaded hole, and the height adjusting rod has one end provided with a first through hole and a second positioning toothed portion arranged around the first through hole, in which the second positioning toothed portion engages with the first positioning toothed portion of the seat of the wrist sheath, and the height adjusting rod is pivotally connected to the seat through a first bolt, while the first bolt is screwed into the first threaded hole of the seat of the wrist sheath after passing through the first through hole of the height adjusting rod.

2. The hand brace of claim 1, wherein the height adjusting rod has a first rod and a second rod, and the first rod has one end provided with the first through hole and the second positioning toothed portion, and an opposite end provided with a second threaded hole and a third positioning toothed portion arranged around the second threaded hole, while the second rod has one end provided with a second through hole and a fourth positioning toothed portion arranged around the second through hole, in which the fourth positioning toothed portion engages with the third positioning toothed portion of the first rod, and the first and second rods are pivotally connected through a second bolt that is received in the second through hole of the second rod and is screwed into the second threaded hole of the first rod.

3. The hand brace of claim 2, wherein the second rod has an opposite end provided with a toothed hole, and the length adjusting rod has a toothed shaft that is connected to the joint portion and fittingly received in the toothed hole.

4. The hand brace of claim 3, wherein the second rod of the height adjusting rod has a third threaded hole radially communicated with the toothed hole, and the second rod of the height adjusting rod are combined with the toothed shaft of the length adjusting rod through a third bolt that is screwed into the third threaded hole of the second rod and props against the toothed shaft of the length adjusting rod.

5. The hand brace of claim 4, wherein the finger support has a cradle and a joint member, in which the cradle has one end provided with a third through hole and a fifth positioning toothed portion arranged around the third through hole, and the joint member has one end pivotally connected to the joint portion of the length adjusting rod, and an opposite end provided with a fourth threaded hole and a sixth positioning toothed portion arranged around the fourth threaded hole, the sixth positioning toothed portion engaging with the fifth positioning toothed portion of the cradle, the cradle being pivotally connected to the joint member through a fourth bolt, the fourth bolt passing through the third through hole of the cradle and being screwed into the fourth threaded hole of the joint member.

6. The hand brace of claim 2, wherein the finger support has a cradle and a joint member, in which the cradle has one end provided with a third through hole and a fifth positioning toothed portion arranged around the third through hole, and the joint member has one end pivotally connected to the joint portion of the length adjusting rod, and an opposite end provided with a fourth threaded hole and a sixth positioning toothed portion arranged around the fourth threaded hole, the sixth positioning toothed portion engaging with the fifth positioning toothed portion of the cradle, the cradle being pivotally connected to the joint member through a fourth bolt, the fourth bolt passing through the third through hole of the cradle and being screwed into the fourth threaded hole of the joint member.

7. The hand brace of claim 3, wherein the finger support has a cradle and a joint member, in which the cradle has one end provided with a third through hole and a fifth positioning toothed portion arranged around the third through hole, and the joint member has one end pivotally connected to the joint portion of the length adjusting rod, and an opposite end provided with a fourth threaded hole and a sixth positioning toothed portion arranged around the fourth threaded hole, the sixth positioning toothed portion engaging with the fifth positioning toothed portion of the cradle, the cradle being pivotally connected to the joint member through a fourth bolt, the fourth bolt passing through the third through hole of the cradle and being screwed into the fourth threaded hole of the joint member.

8. The hand brace of claim 1, wherein the finger support has a cradle and a joint member, in which the cradle has one end provided with a third through hole and a fifth positioning toothed portion arranged around the third through hole, and the joint member has one end pivotally connected to the joint portion of the length adjusting rod, and an opposite end provided with a fourth threaded hole and a sixth positioning toothed portion arranged around the fourth threaded hole, the sixth positioning toothed portion engaging with the fifth positioning toothed portion of the cradle, the cradle being pivotally connected to the joint member through a fourth bolt, the fourth bolt passing through the third through hole of the cradle and being screwed into the fourth threaded hole of the joint member.

9. A hand brace, comprising:
a wrist sheath; and
a finger holder, having a height adjusting rod, a length adjusting rod, and a finger support, the height adjusting rod having one end pivotally connected to an outer lateral surface of the wrist sheath, the length adjusting rod being connected to an opposite end of the height adjusting rod in an axially movable manner and having a joint portion, and the finger support being pivotally connected to the joint portion of the length adjusting rod;
wherein the finger support has a cradle and a joint member, in which the cradle has one end provided with a third through hole and a fifth positioning toothed portion arranged around the third through hole, and the joint member has one end pivotally connected to the joint portion of the length adjusting rod, and an opposite end provided with a fourth threaded hole and a sixth positioning toothed portion arranged around the fourth threaded hole, the sixth positioning toothed portion engaging with the fifth positioning toothed portion of the cradle, the cradle being pivotally connected to the joint member through a fourth bolt, the fourth bolt passing through the third through hole of the cradle and being screwed into the fourth threaded hole of the joint member.

* * * * *